United States Patent
Namin et al.

(10) Patent No.: US 10,123,876 B2
(45) Date of Patent: Nov. 13, 2018

(54) COHESIVE BONE COMPOSITION

(71) Applicant: Vivex Biomedical Inc., Atlanta, GA (US)

(72) Inventors: Shabnam Namin, Miami, FL (US); Wendy W. Weston, Miami, FL (US); Edgar S. Maldonado, Miami, FL (US); Silvia Daniela Gonzales, Miam, FL (US)

(73) Assignee: Vivex Biomedical, Inc., Atlanta, GA (US)

( * ) Notice: Subject to any disclaimer, the term of this patent is extended or adjusted under 35 U.S.C. 154(b) by 15 days.

(21) Appl. No.: 15/647,995

(22) Filed: Jul. 12, 2017

(65) Prior Publication Data

US 2017/0312081 A1     Nov. 2, 2017

Related U.S. Application Data

(62) Division of application No. 15/136,534, filed on Apr. 22, 2016, now Pat. No. 9,788,950.

(51) Int. Cl.
*A61F 2/28*  (2006.01)
*A61L 27/36* (2006.01)
*A61L 27/50* (2006.01)

(52) U.S. Cl.
CPC ............ *A61F 2/28* (2013.01); *A61L 27/3608* (2013.01); *A61L 27/3691* (2013.01); *A61L 27/50* (2013.01); *A61F 2002/2835* (2013.01); *A61L 2430/02* (2013.01)

(58) Field of Classification Search
CPC ................ A61F 2/28; A61F 2002/2817; A61F 2002/2835; A61F 2002/2839; A61F 2002/2842; A61F 2002/30059; A61L 27/36; A61L 27/3604; A61L 27/3608; A61L 27/3691

See application file for complete search history.

(56) References Cited

U.S. PATENT DOCUMENTS

| | | |
|---|---|---|
| 3,458,397 A | 7/1969 | Myers et al. |
| 4,172,128 A | 10/1979 | Thiele et al. |
| 4,440,750 A | 4/1984 | Glowacki et al. |
| 5,073,373 A | 12/1991 | Oleary et al. |
| 5,236,456 A | 8/1993 | Oleary et al. |
| 5,486,359 A | 1/1996 | Caplan et al. |
| 5,490,937 A | 2/1996 | VanReis |
| 5,531,791 A | 7/1996 | Wolfinbarger |
| 5,733,542 A | 3/1998 | Haynesworth et al. |
| 6,432,436 B1 | 8/2002 | Gertzman et al. |

(Continued)

OTHER PUBLICATIONS

Chu Chang Chua, Deborah Ceiman, and Roger L. Ladda; "Transforming Growth Factors Released From Kirsten Sarcoma Virus Transformed Cells Do Not Compete for Epidermal Growth Factor Membrane Receptors"; Journal of Cellular Physiology 117:116-122 (1983).

(Continued)

*Primary Examiner* — Alvin Stewart
(74) *Attorney, Agent, or Firm* — David L. King

(57) ABSTRACT

A cohesive bone composition is made from a moldable bone composition intermixed with a bone gel composition. The cohesive bone composition is made from human cadaver bone. A fluid can be added, the fluid may also be laden with cells.

3 Claims, 13 Drawing Sheets

(56) References Cited

U.S. PATENT DOCUMENTS

| | | | |
|---|---|---|---|
| 6,437,018 B1 * | 8/2002 | Gertzman | C08L 5/08 523/116 |
| 6,458,375 B1 * | 10/2002 | Gertzman | A61F 2/28 424/422 |
| 6,576,249 B1 | 6/2003 | Gendler et al. | |
| RE38,522 E | 5/2004 | Gertzman et al. | |
| 6,911,212 B2 | 6/2005 | Gertzman et al. | |
| 6,998,135 B1 | 2/2006 | Sunwoo et al. | |
| 7,015,037 B1 | 3/2006 | Furcht et al. | |
| 7,019,192 B2 | 3/2006 | Gertzman et al. | |
| 7,045,141 B2 | 5/2006 | Merboth et al. | |
| 7,067,123 B2 | 6/2006 | Gomes et al. | |
| RE39,587 E | 4/2007 | Gertzman et al. | |
| 7,488,348 B2 | 2/2009 | Truncale et al. | |
| 7,659,118 B2 | 2/2010 | Furcht et al. | |
| 7,847,072 B2 | 12/2010 | Thorne | |
| 7,879,103 B2 | 2/2011 | Gertzman et al. | |
| RE42,208 E | 3/2011 | Truncale et al. | |
| 7,901,457 B2 | 3/2011 | Truncale et al. | |
| 8,048,443 B2 * | 11/2011 | Benedict | A61L 27/28 424/426 |
| 8,075,881 B2 | 12/2011 | Verfaillie et al. | |
| RE43,258 E | 3/2012 | Truncale et al. | |
| 8,221,500 B2 | 7/2012 | Truncale et al. | |
| 8,292,968 B2 | 10/2012 | Truncale et al. | |
| 8,328,876 B2 * | 12/2012 | Behnam | A61L 27/227 424/422 |
| 8,354,370 B2 | 1/2013 | Kopen et al. | |
| 8,394,419 B2 | 3/2013 | Borden | |
| 8,734,525 B2 * | 5/2014 | Behnam | A61L 27/3608 424/422 |
| 8,784,908 B1 | 7/2014 | Anderson | |
| 8,834,928 B1 | 9/2014 | Truncale et al. | |
| 9,017,740 B1 | 4/2015 | Anderson | |
| 9,138,508 B2 | 9/2015 | Borden | |
| 9,138,509 B2 | 9/2015 | Sunwoo et al. | |
| 9,192,695 B2 | 11/2015 | Shi | |
| 9,554,920 B2 * | 1/2017 | Wei | A61F 2/28 |
| 9,579,421 B2 | 2/2017 | Bhat | |
| 9,788,950 B1 * | 10/2017 | Weston | A61F 2/28 |
| 9,913,676 B2 * | 3/2018 | Schlachter | A61F 2/28 |
| 2001/0039456 A1 | 11/2001 | Boyer, II | |
| 2002/0018796 A1 * | 2/2002 | Wironen | A61F 2/28 424/423 |
| 2002/0192263 A1 * | 12/2002 | Merboth | C08L 5/08 424/426 |
| 2003/0059414 A1 | 3/2003 | Ho et al. | |
| 2003/0065400 A1 * | 4/2003 | Beam | A61L 27/12 623/23.51 |
| 2003/0143258 A1 * | 7/2003 | Knaack | A61F 2/28 424/426 |
| 2003/0206937 A1 * | 11/2003 | Gertzman | A61K 35/32 424/426 |
| 2004/0058412 A1 | 3/2004 | Ho et al. | |
| 2004/0197373 A1 * | 10/2004 | Gertzman | C08L 5/08 424/423 |
| 2004/0230303 A1 * | 11/2004 | Gomes | A61F 2/28 623/16.11 |
| 2005/0181502 A1 | 8/2005 | Furcht et al. | |
| 2006/0004189 A1 | 1/2006 | Gandy | |
| 2006/0204544 A1 * | 9/2006 | Sunwoo | A61F 2/28 424/423 |
| 2007/0049739 A1 | 3/2007 | Troxel | |
| 2007/0178158 A1 * | 8/2007 | Knaack | A61K 31/728 424/484 |
| 2007/0202190 A1 * | 8/2007 | Borden | A61K 35/32 424/549 |
| 2007/0524177 | 9/2007 | Ho et al. | |
| 2009/0024223 A1 | 1/2009 | Chen | |
| 2009/0074871 A1 * | 3/2009 | Sunwoo | A61L 27/3608 514/1.1 |
| 2009/0155378 A1 * | 6/2009 | Behnam | A61L 27/3608 424/549 |
| 2009/0253810 A1 * | 10/2009 | Katz | A61K 35/32 514/773 |
| 2010/0203155 A1 * | 8/2010 | Wei | A61F 2/30 424/549 |
| 2012/0205274 A1 * | 8/2012 | Sunwoo | A61K 6/08 206/438 |
| 2013/0195810 A1 | 8/2013 | Crawford et al. | |
| 2014/0005793 A1 | 1/2014 | Koford | |
| 2014/0010890 A1 * | 1/2014 | Borden | A61F 2/07 424/549 |
| 2014/0030235 A1 | 1/2014 | Varney et al. | |
| 2015/0012107 A1 | 1/2015 | Koford et al. | |
| 2016/0030639 A1 | 2/2016 | Shi | |
| 2016/0135954 A1 * | 5/2016 | Schlachter | A61F 2/28 623/23.63 |
| 2016/0361171 A1 | 12/2016 | Wang | |
| 2016/0361467 A1 | 12/2016 | Klimek | |
| 2017/0007739 A1 * | 1/2017 | Reves | A61L 27/24 |
| 2017/0119929 A1 | 5/2017 | Bhat | |

OTHER PUBLICATIONS

Yawei Liu, Anders Kalen, Olof Risto & Ola Wahlstrom; "Time- and pH-dependent release of PDGF and TGF-11 from platelets <emph type="2" >in vitro</emph>"; pp. 233-237 Platelets vol. 14, Issue 4, 2003 ; Published online: Jul. 7, 2009.

Trinity Elite, product, sales brochure, TT-1515, Orthofix Holdings Inc, Oct. 2015.

Osteocel bone grail web page, http://www.nuvasive.com/patient-solutions/nuvasive-integrated-surgical-solutions/osteocel-bone-grafl/; 2016.

* cited by examiner

FIG. 3      10, 30      11
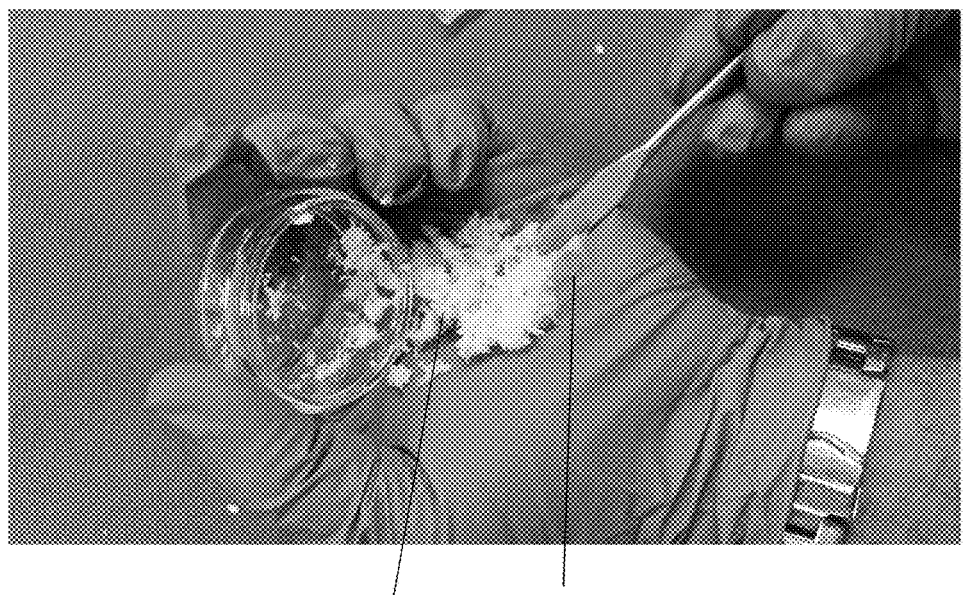
FIG. 4      10, 30      11

COHESIVE BONE COMPOSITION

RELATED APPLICATIONS

This application is a division of co-pending U.S. application Ser. No. 15/136,534 filed on Apr. 22, 2016 entitled, "Cohesive Bone Composition".

TECHNICAL FIELD

This invention is a moldable cohesive bone composition made from a mineralized and demineralized bone composition mixed with a demineralized bone composition in the form of a gel. More specifically, a cohesive composition that can be formed into a molded shape retaining structure by adding appropriate compatible fluid for bone repair and a method of manufacture and use of said composition.

BACKGROUND OF THE INVENTION

The manufacture and use of bone allografts from bone tissue is well known. The use of particles of various specific sizes and distributions have been determined to have beneficial characteristics for new bone growth in the treatment of osseous defects and bone voids.

The issue of getting the repair composition to stay in position has been addressed for various formulations made into malleable paste or putty by the addition of collagen or other gelatinous materials.

The present invention provides an improvement over those prior art materials.

SUMMARY OF THE INVENTION

A cohesive bone composition having a moldable bone composition intermixed with a bone gel composition.

The moldable bone composition consists of a mixture of: cortical bone and cancellous bone. The cortical bone is formed in three portions, a mineralized shaving portion and a demineralized shaving portion and a mineralized powder portion. The cancellous bone is formed in a mineralized crushed cancellous portion. The portions are free-dried and mixed together to form a freeze-dried moldable bone composition. When subjected to a fluid, the composition can be molded to a desired shape. The crushed cancellous bone is made from freeze-dried morselized cancellous ground to a size of 1000 to 1700 microns. The cortical bone powder is ground to 300 microns or less. The cortical shavings are long thin strips cut from cortical bone plates having a length of greater than 5 cm. The cortical shavings are strands having a length greater than 3 mm. The mixture has a percentage of demineralized cortical bone shaving portion either by weight or volume in the range of 15 to 25%; a percentage of mineralized dry cortical bone shaving either by weight or volume in the range of 70 to 50%; a percentage of mineralized dry cortical bone powder either by weight or volume in the range of 5 to 15% and a percentage of dry crushed cancellous either by weight or volume in the range of 5 to 15%.

The preferred moldable bone composition has a percentage of 20% demineralized cortical bone shaving, 60% dry mineralized cortical bone shaving, 10% dry cortical bone powder and 10% dry crushed cancellous. The composition is formed as a freeze-dried material packaged in jars wherein the packaged mixture is stored at room temperature or frozen.

The bone gel composition consists of cortical bone. The cortical bone is made from cut pieces freeze-dried then ground into particles and demineralized then freeze-dried. A volume of the particles is placed in a solution of sterile water to create a mixture, the water volume being twice the second portion, the mixture is autoclaved under heat and pressure to form a gelatin, the resulting bone gel is placed in jars and may be kept at room temperature frozen for later use. The cortical bone has the cut pieces having a width, a length and a thickness in the range of 1 to 4 mm. The cortical bone pieces are ground to a particle size up to 125 microns.

A volume of the moldable bone composition is intermixed with a volume of bone gel composition forming the cohesive bone composition. In one embodiment, a fluid can be added to the cohesive bone mixture. The fluid can be laden with cells if so desired. The fluid can be sterile water, lactated Ringer's solution, saline solution, normal saline, plasma, blood or any other commonly used material.

The method of manufacturing the cohesive bone composition includes a method of making the moldable bone composition and a method of making the bone gel composition and mixing them together with or without addition of a fluid.

The method of manufacturing a moldable bone composition has the steps of: cutting cortical bone plates into long pieces; shaving the cortical bone plates to form cortical strands or shavings 3 mm or greater in length; demineralizing a first portion of the cortical shavings; grinding another portion of the cortical shavings; resulting the cortical bone having three portions, a demineralized cortical shavings portion, a mineralized cortical shavings portion and a powered cortical portion; cutting and grinding cancellous bone to form a portion of mineralized crushed cancellous bone from a size of 1000 to 1700 microns; freeze-drying each portion; and mixing together all of the portions in a predetermined ratio to form a freeze-dried composition.

The method of making a bone gel composition consisting of cortical bone comprises the steps of: preparing cortical bone by cutting the cortical bone into pieces, freeze-drying the pieces and then grinding into particles and demineralizing the ground particles and the freeze-drying the demineralized ground particles to form DBM particles; autoclaving a volume of the DBM particles mixed with sterile water in a 2:1 ratio by volume for a predetermined time at a pre-set temperature and pressure to form a gelatin; cooling the gelatin to form a bone gel; and packaging the resulting bone gel and storing the packaged bone gel.

Definitions

Cohesiveness is defined as the capacity of DBM aseptic paste to maintain its shape while immersed in normal saline or water for a minimum of one minute.

DBM—Demineralized Bone Matrix.

Cryopreserved—Tissue frozen with the addition of, or in a solution containing, a cryoprotectant agent.

Freeze Dried/Lyophilized—Tissue dehydrated for storage by conversion of the water content of frozen tissue to a gaseous state under vacuum that extracts moisture.

Malleability is the ability of DBM aseptic paste to be molded into different shapes with no visible cracks.

Normal Saline—0.9% Sodium Chloride Solution.

PBS—Phosphate Buffered Saline.

SRI—an equipment sterilization service company.

BRIEF DESCRIPTION OF THE DRAWINGS

The invention will be described by way of example and with reference to the accompanying drawings in which:

FIG. 3 is a photograph of a gloved hand holding the moldable bone composition in a container with the bone gel composition spread on the palm area.

FIG. 4 is a photograph of the freeze-dried moldable bone composition from the container being mixed with the bone gel composition.

FIG. 21A is an exemplary formulation, FIG. 21B a weight range, and 21C shows an exemplary volume.

DETAILED DESCRIPTION OF THE INVENTION

Figure 1:
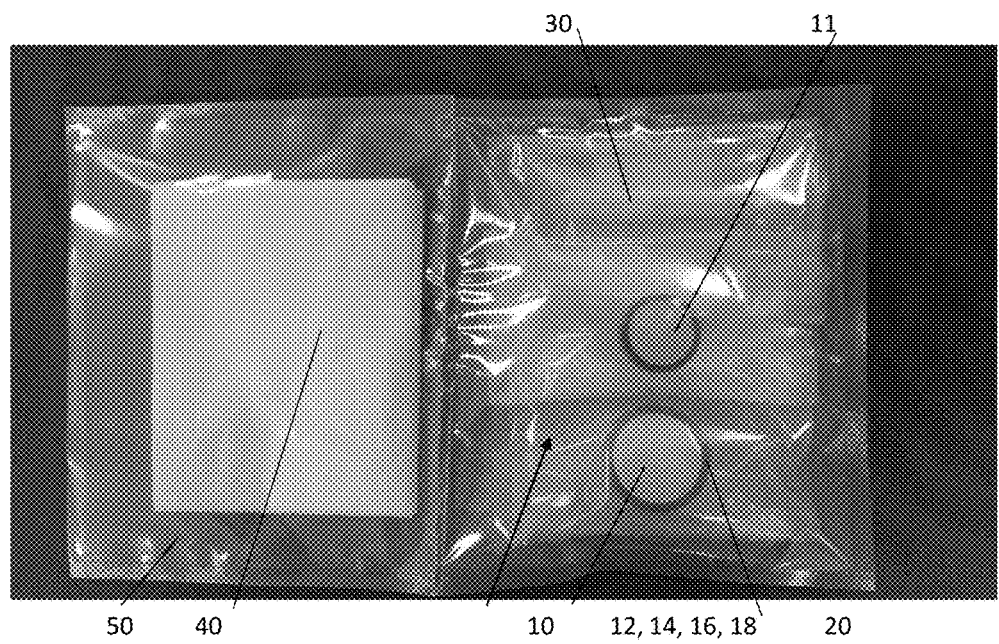
FIG. 1 shows a photograph of the cohesive bone composition showing the moldable bone composition, the bone gel composition and a vial of fluid in a container packaged in a clear sealed bag.

The present invention cohesive bone composition 100 encompasses the manufacturing of an aseptic moldable bone composition 10 and a bone gel composition 11 derived from human cadaveric cortical and cancellous bone. Cortical and cancellous bone is obtained from male or female donors. Full body donors with no joint replacements are preferred. The donors' medical and social history are screened for medical conditions such as osteoporosis and alcohol abuse, which may hinder the intended purpose of the final product. The demineralization process of bone tissue exposes morphogenetic proteins and other intrinsic growth factors involved in providing the osteoinductive signal to form new bone. Therefore, the application of cohesive bone composition aseptic product is intended to aid in the treatment of osseous defects and bone voids. The moldable bone 10 and bone gel 11 compositions when mixed together forms the cohesive bone composition 100 which is ready for implantation and may or may not require thawing. At room temperature with appropriate fluid 30 added, cohesive bone composition 100 is moldable. First, the moldable bone composition is described followed by the bone gel and then the mixture of the two.

Figure 2:
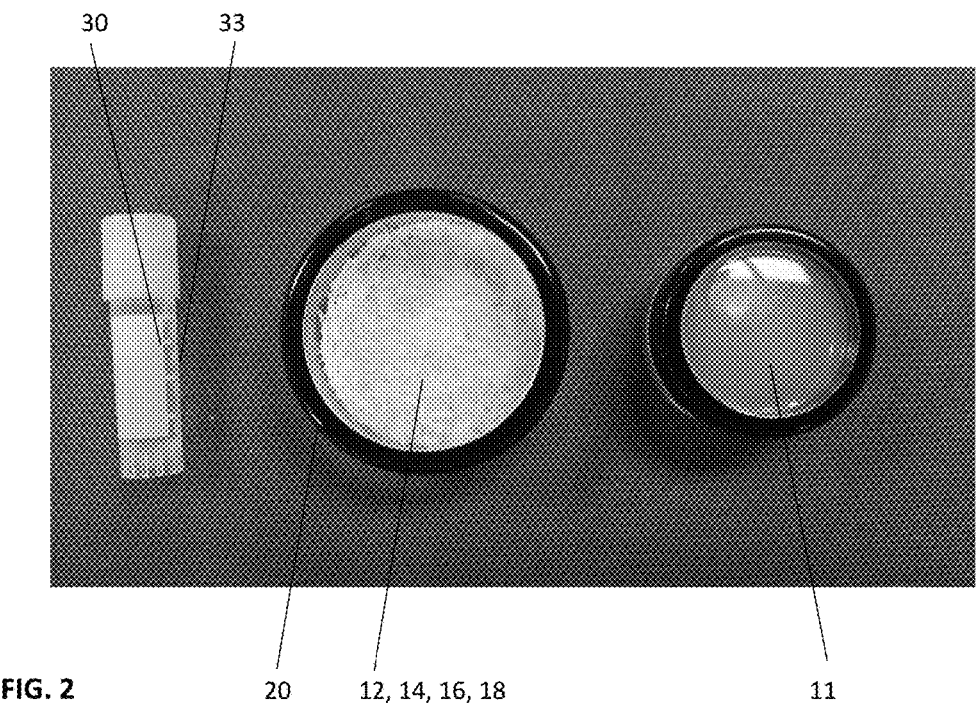
FIG. 2 is a photograph of the moldable bone composition and bone gel composition and the fluid vial from FIG. 1.

The moldable bone composition 10 is entirely derived from aseptic allograft cortical and cancellous bone. The cortical bone is aseptically cleaned, cut and shaved in order to obtain cortical bone shavings. Part of the cortical bone shavings are demineralized. The cancellous bone is cleaned, cut and crushed. Moldable bone composition is prepared by mixing mineralized shavings and powder, demineralized cortical shavings and crushed cancellous bone. As shown in FIG. 1, the moldable bone composition 10 products of 2.5, 5 or 10 cc are distributed into containers, packaged in final packaging, as shown in FIG. 1 or with the sealed bag 50 removed as shown in FIG. 2 and stored at room temperature or frozen until distribution to the end user.

Figure 7:
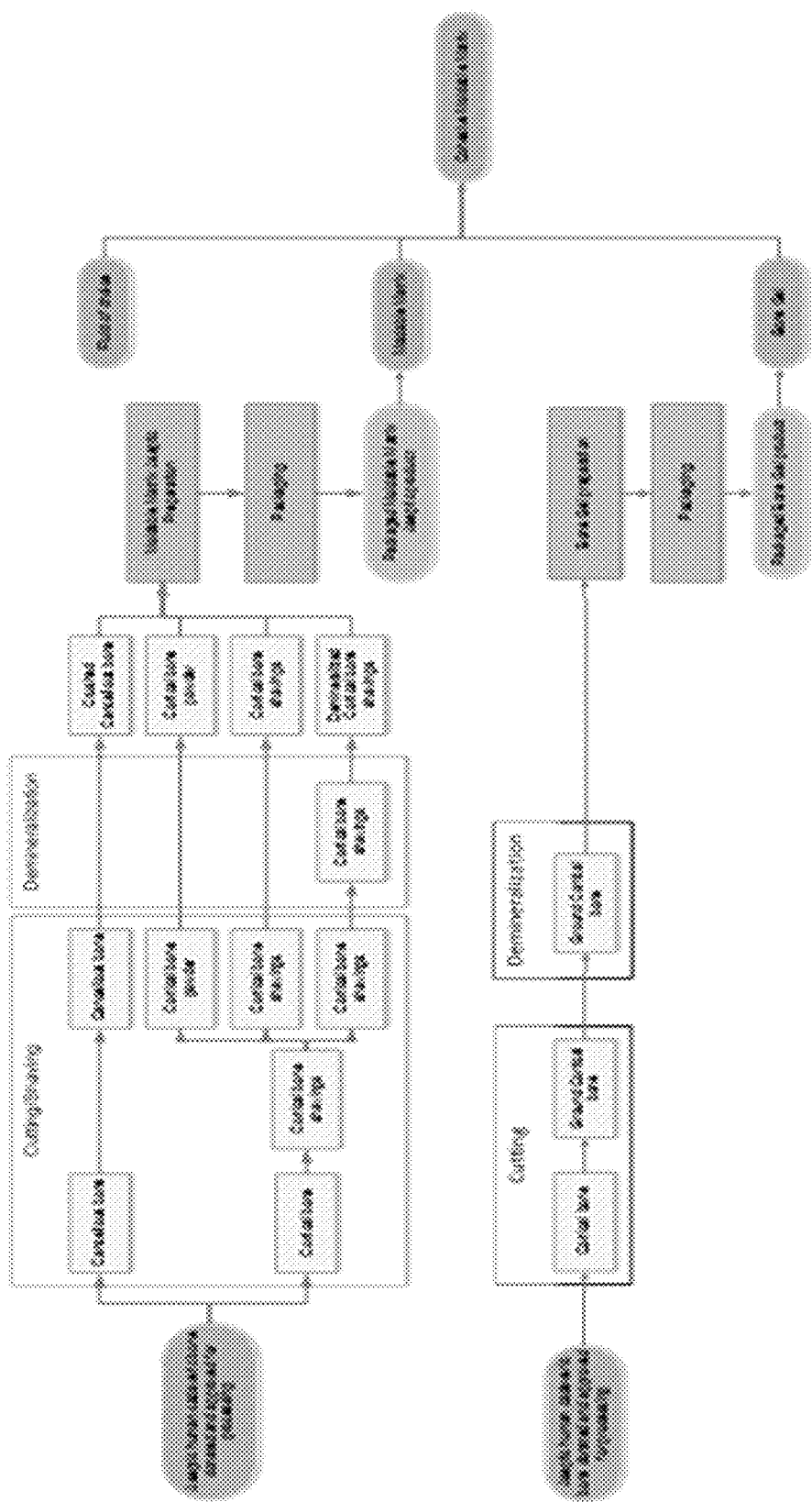
FIG. 7 is a schematic illustration of the cohesive bone composition manufacturing process outline.

The overall manufacturing process outline for the cohesive bone composition with moldable bone and bone gel composition products is shown in FIG. 7. With reference to the moldable bone composition which is described first, the input of the process is the donated and approved for processing aseptic human cadaveric cortical and cancellous bone immediately frozen after recovery. Once the cortical and cancellous bone has been processed, the output is the packaged moldable bone composition product. The moldable bone composition process itself has been divided into six subprocesses with their own respective inputs and outputs. The breakdowns of these individual subprocesses are described, as shown in FIGS. 8-16.

Figure 8:
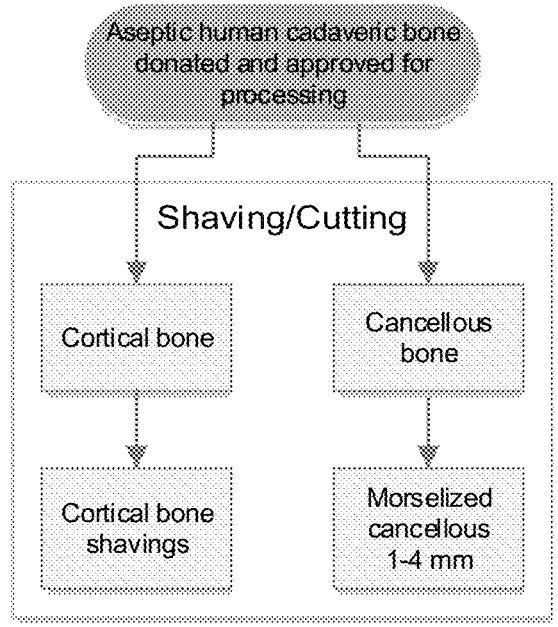
FIG. 8 shows the subprocess of shaving/cutting taken from FIG. 7.

The Shaving/Cutting subprocess is illustrated schematically in FIG. 8.

Prior to cutting the donated and approved for processing aseptic human cadaveric cortical and cancellous bone, all extraneous material such as muscle fibers, adipose tissue, and periosteum are removed from the tissue. Bones are then rinsed a minimum of 3 times with physiological grade normal saline (0.9% Sodium Chloride). Using a band saw, the bones are cut in a manner that the cortical and cancellous portions are separated. Cortical bone shafts are cut in half longitudinally and placed in basins with normal saline. Cancellous bone cut into pieces and crushed. Further cleaning and cutting of cortical and cancellous bone is as detailed below.

Cortical Bone Shavings: Cortical bone plates are cut into approximately 6.5 cm long pieces. The bone plates are placed in a wash can with normal saline. The wash can is wrapped and agitated for 5 to 10 minutes to remove any blood and adipose tissue. Bone tissues are then rinsed with normal saline as often as needed to clean tissue of blood and/or fatty deposits. The bone tissues are shaved using a shaving machine set to produce >3 mm strands. Cortical bone shavings are collected in a basin and rinsed with hydrogen peroxide if required for no more than 10 minutes to remove fat/blood if necessary. Cortical bone shavings are rinsed a minimum of three times with sterile water to remove any residual hydrogen peroxide. The shavings are stored at −80° C. as schematically detailed at the top of FIG. 9.

Cancellous Bone: Cancellous bone is cut into small pieces using a band saw. The small pieces are rinsed a minimum of three times in normal saline and then placed into a metal container with normal saline. The container is wrapped, placed on a shaker and mechanically agitated for 5 to 10 minutes. The bone tissue is then crushed into approximately 1-4 mm pieces using a morselizer. The tissue is rinsed a minimum of three times with normal saline in order to remove any remnants of blood and/or fat deposits. The bone pieces are rinsed with hydrogen peroxide if required for no more than 10 minutes to remove fat/blood. The bone pieces are rinsed a minimum of three times with sterile water to remove any residual hydrogen peroxide. The cancellous bone tissue is placed in a metal cube and stored at −80° C. prior to freeze-drying.

Figure 9:
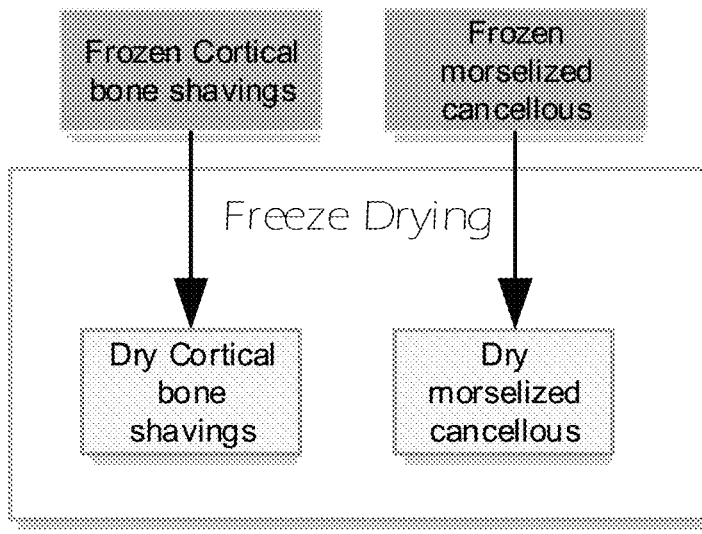
FIG. 9 shows the subprocess of freeze-drying taken from FIG. 7.
Figure 14:
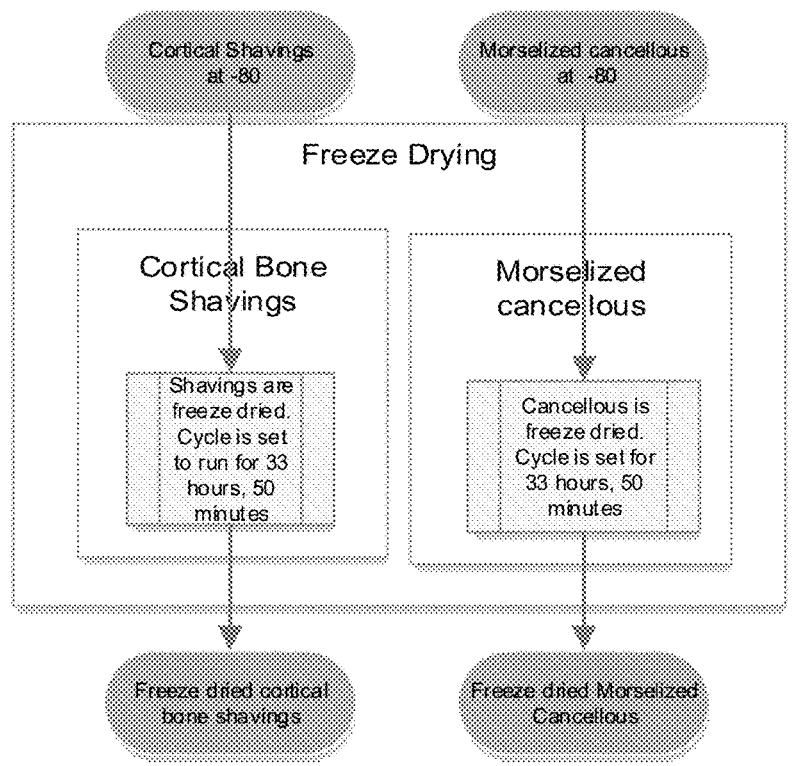
FIG. 14 shows the subprocess of freeze-drying taken from FIG. 7.

The first Freeze-Drying subprocess is shown in FIGS. 9 and 14.

Once the cortical bone shavings and morselized cancellous have been created and separately stored at −80 C, the frozen material is then prepared to undergo the freeze drying process. The shavings and cancellous are placed in metal cubes on sterile drying trays. The drying trays are then placed inside of a freeze dryer which is set to run for 33 hours 50 minutes. This cycle has shown to sufficiently dry the tissue without affecting the structural and chemical properties of the tissue. It is understood the timing can vary based on the equipment and procedures used and the above is exemplary of the preferred process for the inventors' equipment. By sufficiently drying, the inventors intend the moisture content to be less than 10 percent, preferably about 5 percent.

Figure 10:
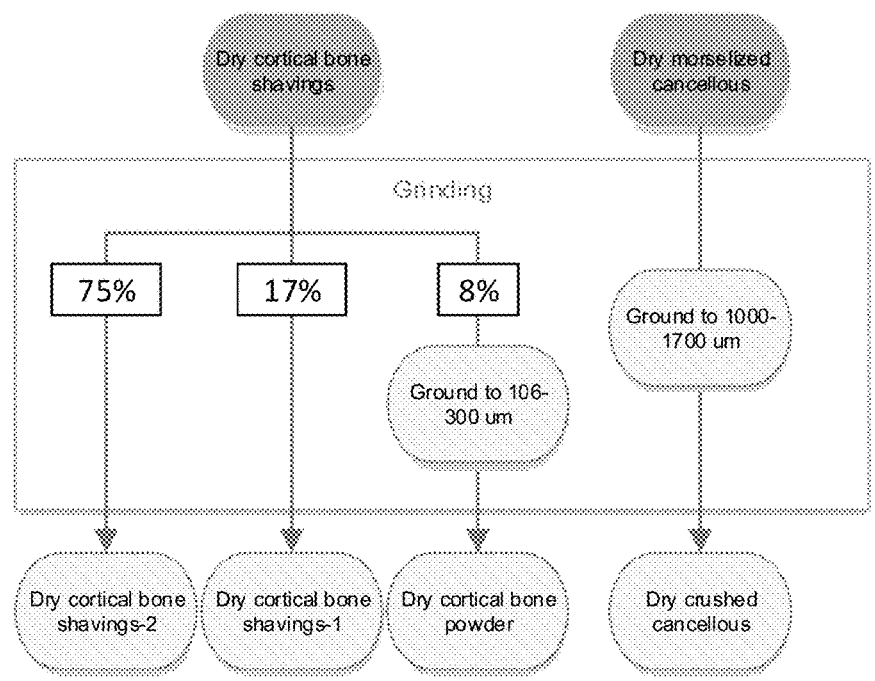
FIG. 10 shows the subprocess of grinding taken from FIG. 7.
Figure 15:
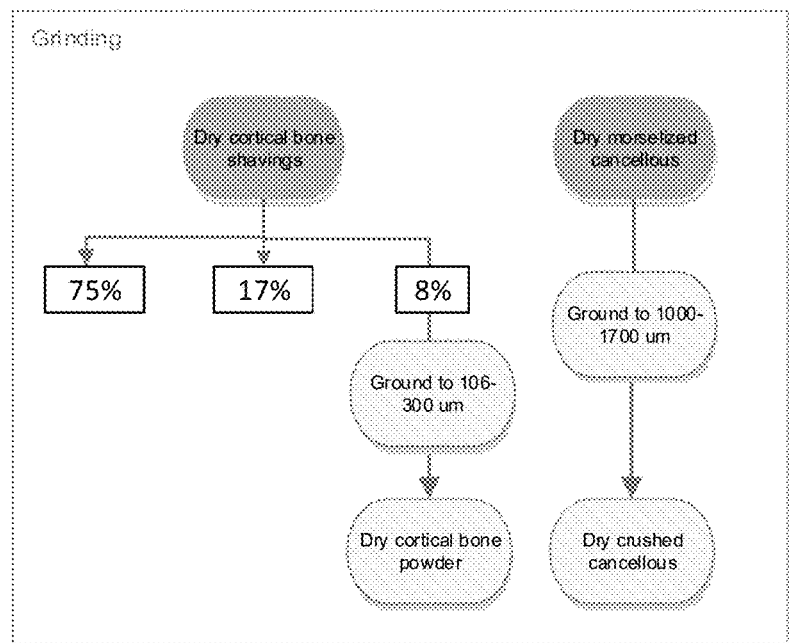
FIG. 15 shows the subprocess of grinding taken from FIG. 7.
Figure 16:
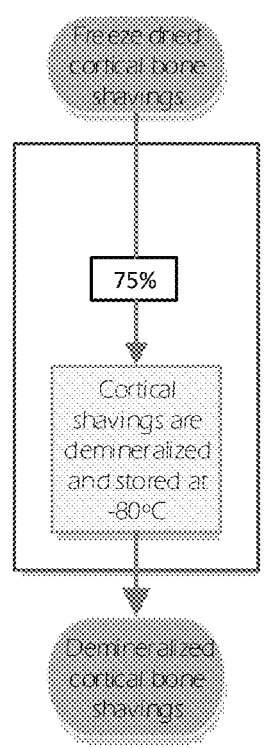
FIG. 16 shows the subprocess of demineralizing cortical bone shavings.

The Grinding subprocess is shown in FIGS. 10 and 15. The dry cortical bone shavings are divided into 3 portions, preferably an exemplary division of 75% (dry cortical bone shavings-2), 17% (dry cortical bone shavings-1) and 8% all by volume. The division can vary within ranges 80-70%; 20-15%; and 15-5% with the understanding the powder should be no less than 5% and the cortical shavings no more than 80% in order for the composition to adequately perform. Only the 8% portion of the dry cortical bone shavings are ground to 106-300 um utilizing a bone grinder. The remaining portions are not ground and move to the next process. The dry morselized cancellous bone is ground to 1000-1700 um utilizing a bone grinder on slow setting. This is called "crushed cancellous".

Figure 11:
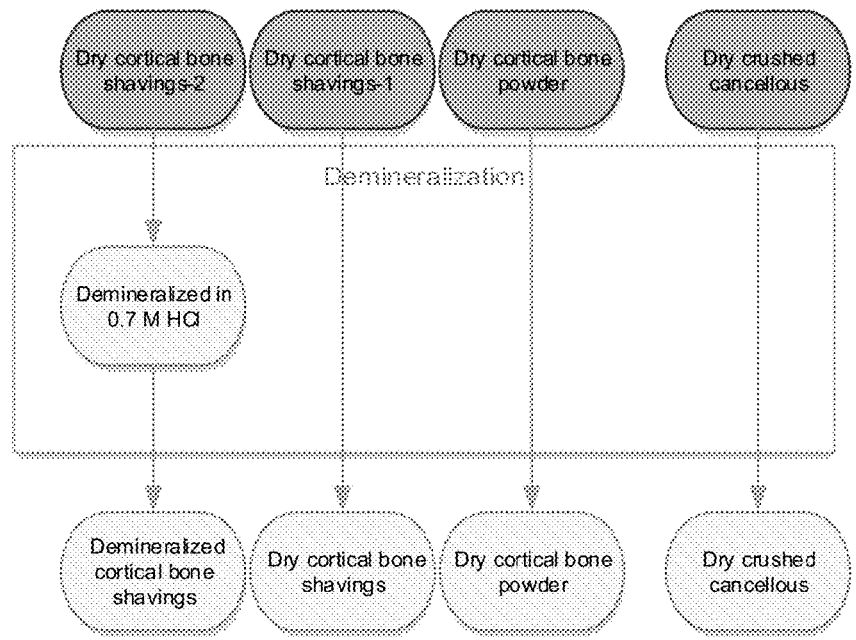
FIG. 11 shows the subprocess of demineralization taken from FIG. 7.

The Demineralizing subprocess is schematically shown in FIG. 11. The dry cortical bone shavings-2 is mixed with 0.7 HCL solution at a 20:1 ratio (20 ml of 0.7 HCL to 1 g of bone). The solution containing the tissue is placed on a magnetic stir plate for 59 minutes. It is understood the timing can vary based on the equipment and procedures used and the above is exemplary of the preferred process for the inventors' equipment. After decanting the liquid, the particulate tissue is mixed with sterile water at a 20:1 ratio (20 ml of sterile water to 1 g of bone). The solution containing the tissue is placed on a magnetic stir plate for 4 minutes. The process of decanting, mixing and incubating for 4 minutes is repeated with PBS solution. After decanting the PBS, the shavings are mixed with sterile water at a 20:1 ratio (20 ml of sterile water to 1 g of bone). The solution containing the tissue is placed on a magnetic stir plate for 9 minutes. The water waste solution is decanted and the demineralized shavings are stored at −80° C.

Figure 12:
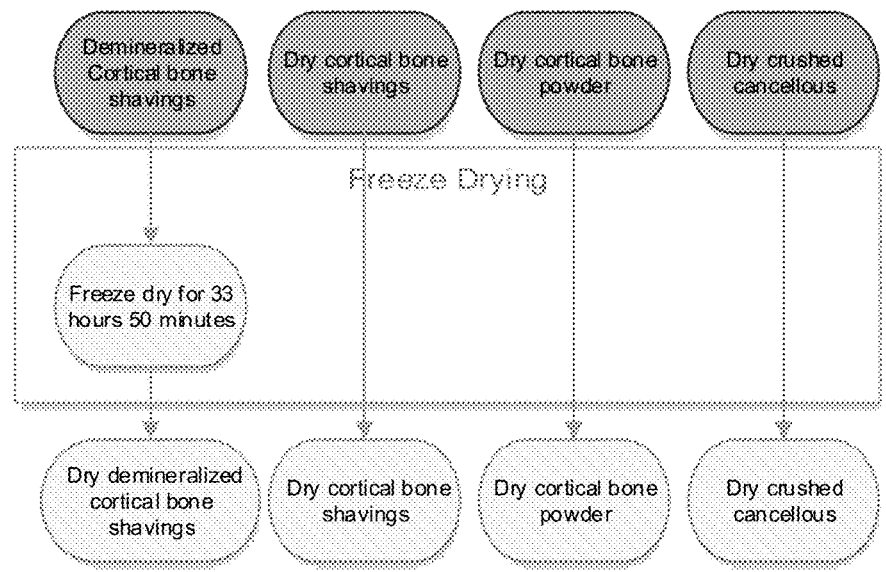
FIG. 12 shows the subprocess of freeze-drying taken from FIG. 7.

The second Freeze-Drying subprocess is shown in FIGS. 12 and 14. The demineralized cortical bone shavings are then prepared to undergo the freeze drying process again. The shavings are placed on separate sterile drying trays. The drying trays are then placed inside of a freeze dryer which is set to run for 33 hours 50 minutes. This cycle has shown to sufficiently dry the tissue without affecting the structural and chemical properties of the tissue.

Figure 13:
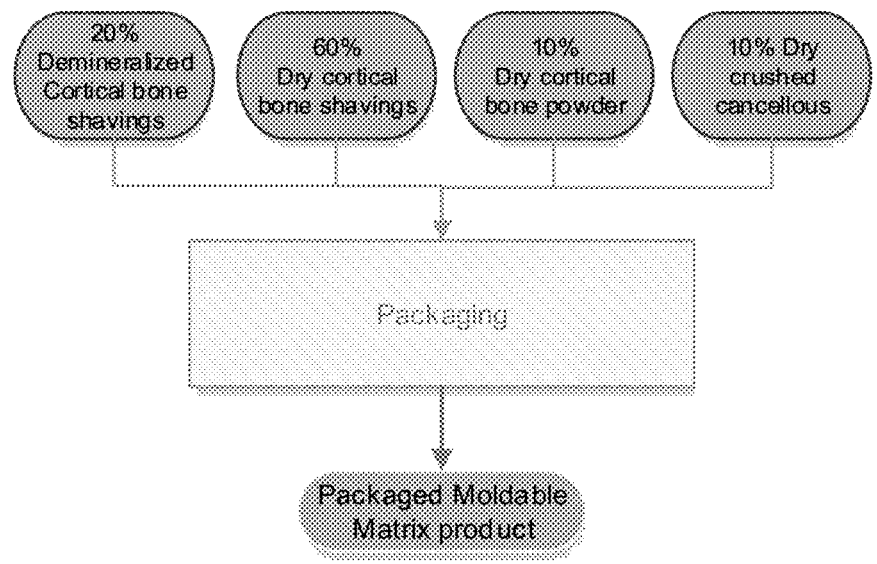
FIG. 13 shows the subprocess of packaging taken from FIG. 7.

The Packaging subprocess is shown in FIG. 13. Final processed mineralized and demineralized cortical shavings, crushed cancellous and cortical powder are combined at preferably an exemplary combination of 20% (0.2 g per 5 cc unit) dry demineralized cortical bone shavings, 60% dry mineralized cortical bone shavings, 10% dry cortical bone powder and 10% dry crushed cancellous and packaged in validated final packaging. The mixture is aseptically measured into jars; each jar closed tightly. The outer packaging used is a chevron type pouch allowing the end user to easily present the sterile inner pouch containing the product to a sterile field. The packaged final product is stored at room temperature or frozen until it is distributed to the end user. It is believed the above combination of the 4 constituent components is an optimum ratio. It is further understood variation of plus or minus 5% in and of the four materials is considered to be within the scope of the present invention such that the final product could have 25-15% dry demineralized cortical bone shavings; 65-55% dry mineralized cortical bone shavings; 15-5% dry cortical bone powder; and 15-5% dry crushed cancellous and are feasible to form the moldable bone composition 10.

The final product when used can be mixed with sterile water, lactated Ringer's solution, saline solution, normal saline, blood, plasma or other suitable liquid to achieve the moldable characteristics needed for the surgical repair of a bone malady. In a related co-pending application attorney docket number DN0257CIP, this mixture is combined with a fluid containing cells including stem cells.

As illustrated in FIG. 7, the manufacturing of bone gel is described hereafter. The bone gel composition 11 derived from human cadaveric cortical bone is now described. Cortical bone is obtained from male or female donors within suitable age groups. Full body donors with no joint replacements are preferred. The donors' medical and social history are screened for medical conditions such as osteoporosis and alcohol abuse, which may hinder the intended purpose of the final product. At ambient temperature, bone gel is gelatinous and cohesive. Therefore, it is intended to serve as a binding agent. Bone gel is ready for use or can be mixed with other products.

The bone gel product is entirely derived from cortical bone. The cortical bone is aseptically recovered, cleaned, cut, morselized or shaved, ground, sieved at different sizes, demineralized and freeze-dried to obtain cortical bone particles. Freeze dried, demineralized, ground cortical bone is then mixed with water. The mix is pressurized and heated to form the Bone Gel. Final Bone Gel 10 products of 2 cc, 4 cc or 8 cc are distributed into containers 20, packaged in final packaging 50, as shown in FIG. 1, and stored at room temperature or frozen until distribution to the end user. The amount of bone gel can vary depending on the application.

The overall manufacturing process for the Bone gel product can be seen in FIG. 7. The input of the process is the donated and approved for processing aseptic human cadaveric cortical bone immediately frozen after recovery. Once the cortical bone has been processed, the output is the packaged Bone gel product. The process itself has been divided into four subprocesses with their own respective inputs and outputs.

Figure 17:
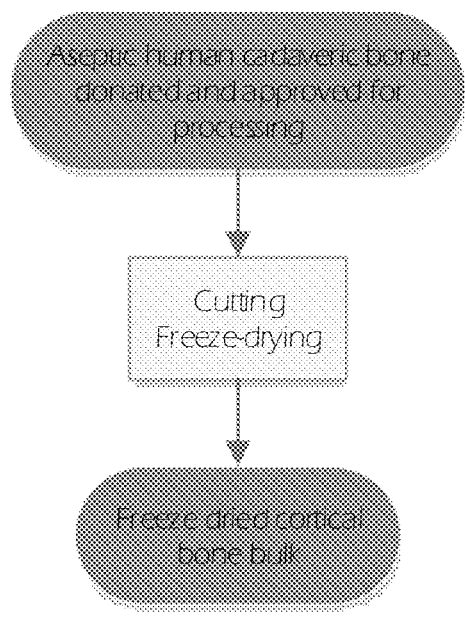
FIG. 17 is a schematic illustration of the subprocess of cutting and freeze-drying the bone gel composition.

The cutting subprocess is schematically shown in FIG. 17.

Prior to cutting the donated and approved for processing human cadaveric cortical bone, all extraneous material such as muscle fibers, adipose tissue, and periosteum are removed from the tissue. Bones are then rinsed a minimum of 3 times with physiological grade Normal Saline (0.9% Sodium Chloride). Using a band saw, the bones are cut in a manner that the cortical and cancellous portions are separated.

The cortical bone is then cut into small pieces using a band saw. The small pieces are rinsed a minimum of three times in Normal Saline and then placed into a metal container with fresh Normal Saline. The container is aseptically wrapped, placed on a shaker and mechanically agitated for 5 to 10 minutes. The bone tissue is then morselized into 1 to 4 mm length and width pieces, respectively, using a morselizer. The tissue is rinsed again a minimum of three times with Normal Saline in order to remove any remnants of blood and/or fat deposits. The bone pieces are rinsed with hydrogen peroxide for no more than 10 minutes to remove fat/blood. The bone pieces are rinsed a minimum of three times with sterile water to remove any residual hydrogen peroxide. Then, the bone tissue is placed in a metal container and stored at −80° C. The frozen bone tissue is freeze dried with a cycle set for 33 hours and 50 minutes. It is understood the timing, ratios and volumes can vary based on the equipment and procedures used and the above is exemplary of the preferred process for the inventors' equipment.

Figure 18:
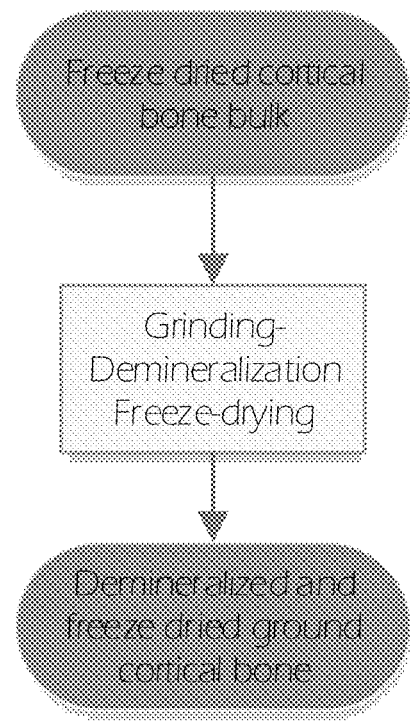
FIG. 18 is a schematic illustration of the subprocess of grinding, demineralization, freeze-drying the bone gel composition.

The Grinding-Demineralization subprocess is shown in FIG. 18.

Once the freeze drying cycle is completed, the cortical bulk is ground and sieved to obtain particle sizes of up to 125 μm, typically 25 to 125 μm. The particulate tissue is demineralized by addition of 0.6 HCL solution at a 20:1 ratio (20 ml of 0.6 HCL to 1 g of bone). The solution containing the tissue is placed on a magnetic stir plate for 19 minutes. After decanting the liquid, the particulate tissue is mixed with sterile water at a 20:1 ratio (20 ml of sterile water to 1 g of bone). The solution containing the tissue is placed on a magnetic stir plate for 4 minutes. The process of decanting, mixing and incubating for 4 minutes is repeated with PBS solution. After decanting the PBS, the particulate tissue is mixed with sterile water at a 20:1 ratio (20 ml of sterile water to 1 g of bone). The solution containing the tissue is placed on a magnetic stir plate for 9 minutes. The water waste solution is decanted and the demineralized particulate tissue is stored at −80° C. The frozen, demineralized particulate tissue is freeze dried for 33 hours 50 minutes. At the end of the freeze drying process, samples can be collected for residual moisture and residual calcium testing. It is understood the timing, ratios and volumes can vary based on the equipment and procedures used and the above is exemplary of the preferred process for the inventors' equipment.

Figure 19:
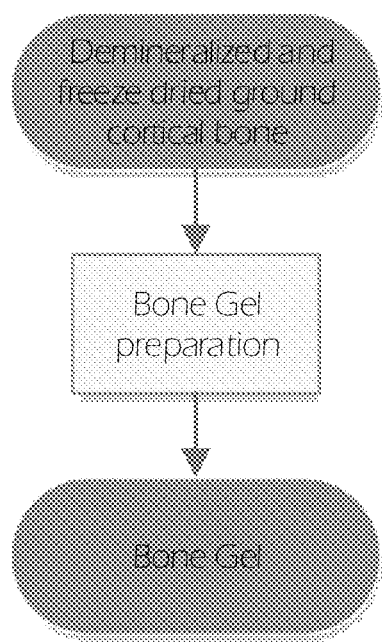
FIG. 19 is a schematic illustration of the subprocess of bone gel preparation.

The Bone Gel Preparation subprocess is shown in FIG. 19.

The demineralized, freeze-dried cortical bone particles can be divided into groups of 100 cc, approximately. Each group is placed in a Pyrex glass bottle and mixed with sterile water. The ratio of sterile water to particles is 2:1 by volume. In order to prepare Bone Gel, the mix is autoclaved for 1.25 hours. The autoclaving process includes conditioning (15 minutes), exposure (30 minutes) and drying (30 minutes). Temperature during the exposure step is 121.1° C. and the pressure is 30.15 psi. After autoclaving is completed, the Bone Gel is aliquoted to jars. It is understood the timing, ratios and volumes can vary based on the equipment and procedures used and the above is exemplary of the preferred process for the inventors' equipment.

Figure 20:
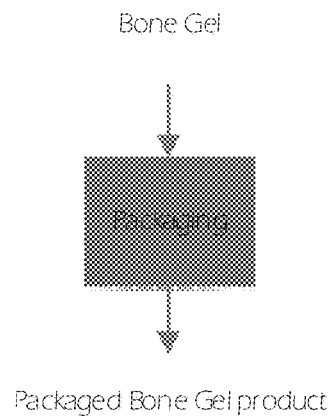
FIG. 20 is a schematic illustration of the subprocess of packaging the bone gel composition.
Figure 21A:
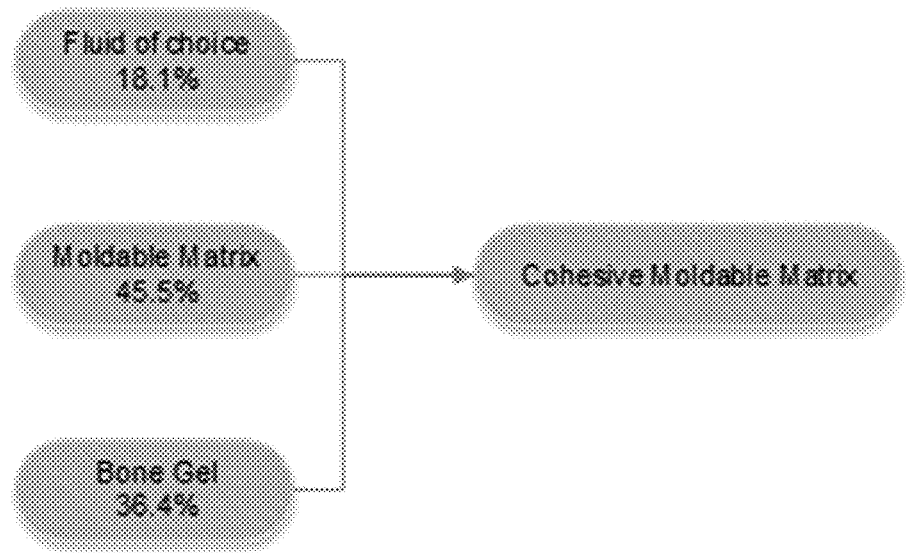
FIGS. 21A, 21B and 21C are diagrams of the cohesive bone composition.
Figure 21B:
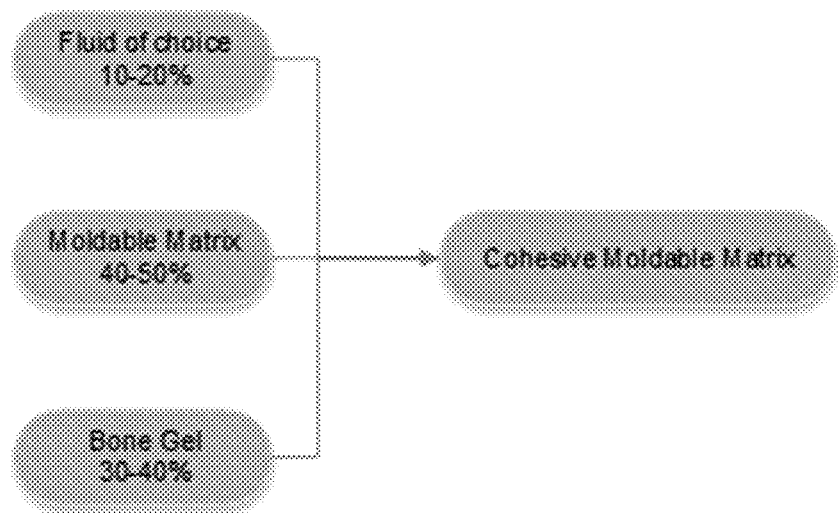
Figure 21C:
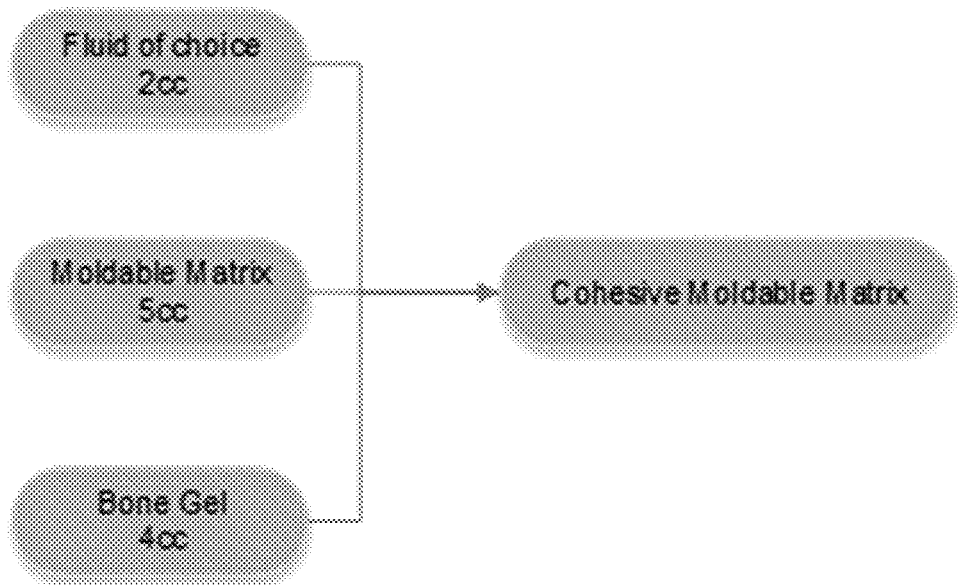

The Packaging subprocess is shown in FIG. 20.

The Bone Gel is packaged in closed containers. The containers have a lid insert 22 secured by a cap 24. The packaged final products are stored at room temperature or frozen until they are distributed to the end user. Batch release is contingent upon final culture results.

The bone gel composition is designed to be mixed with allograft or autograft bone particles, strands, growth factors, bone putty, bone paste, cells, or other bone growth enhancing products.

The cohesive bone composition: After the moldable bone composition and the bone gel are separately prepared, they can be combined together with the addition of a volume of fluid to form the cohesive composition. The fluid can be laden with cells if so desired. The fluid can be sterile water, lactated Ringer's solution, normal saline, plasma, blood or any other commonly used material.

Figure 5:
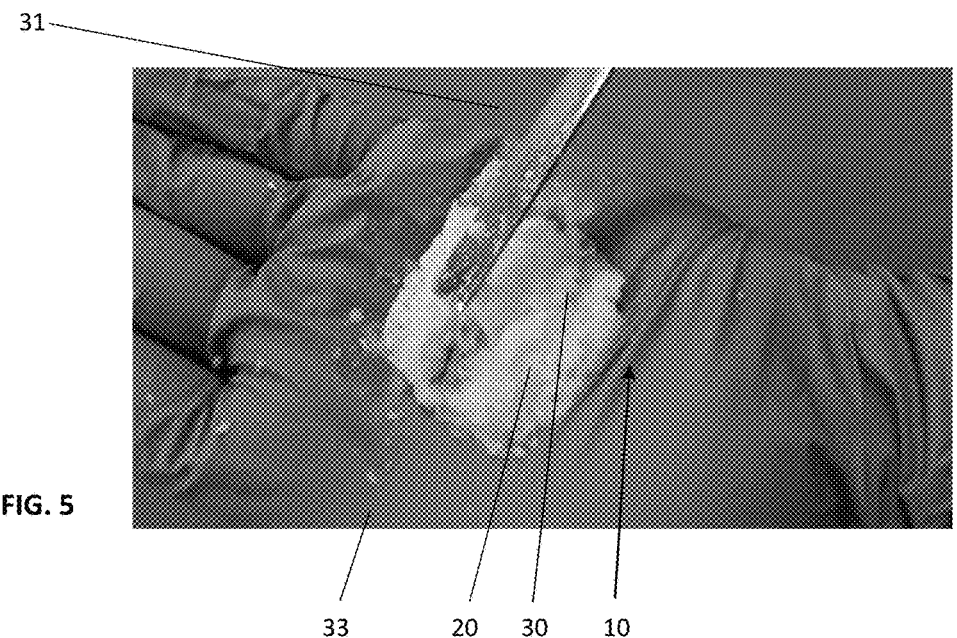
FIG. 5 is a photograph of the cohesive bone composition after being mixed.
Figure 6A:
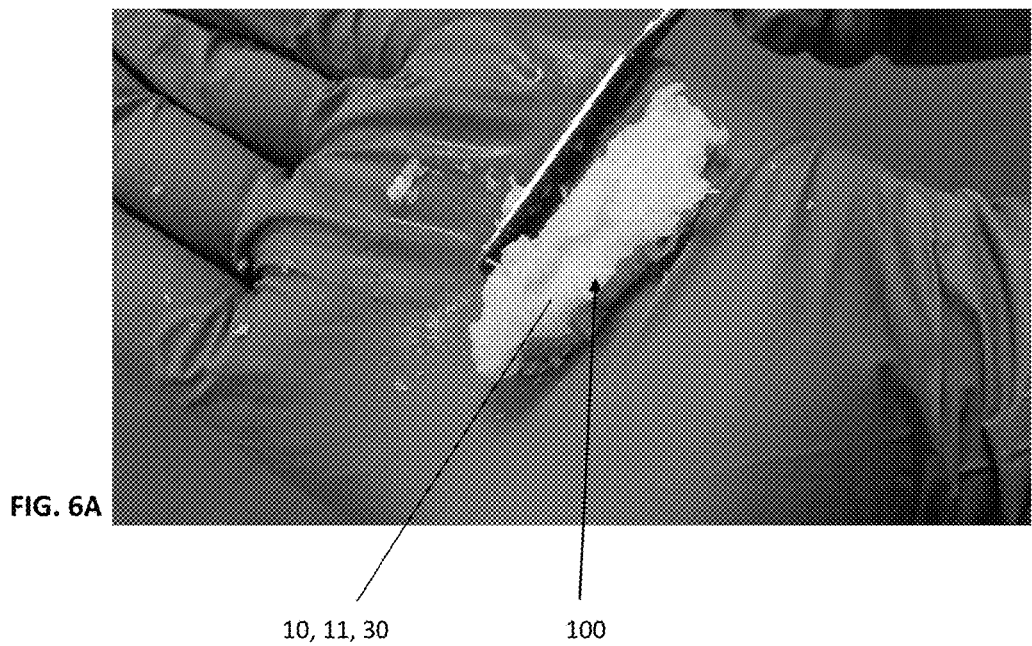
FIG. 6A is a photograph of the cohesive bone composition being shaped with a tool.
Figure 6B:
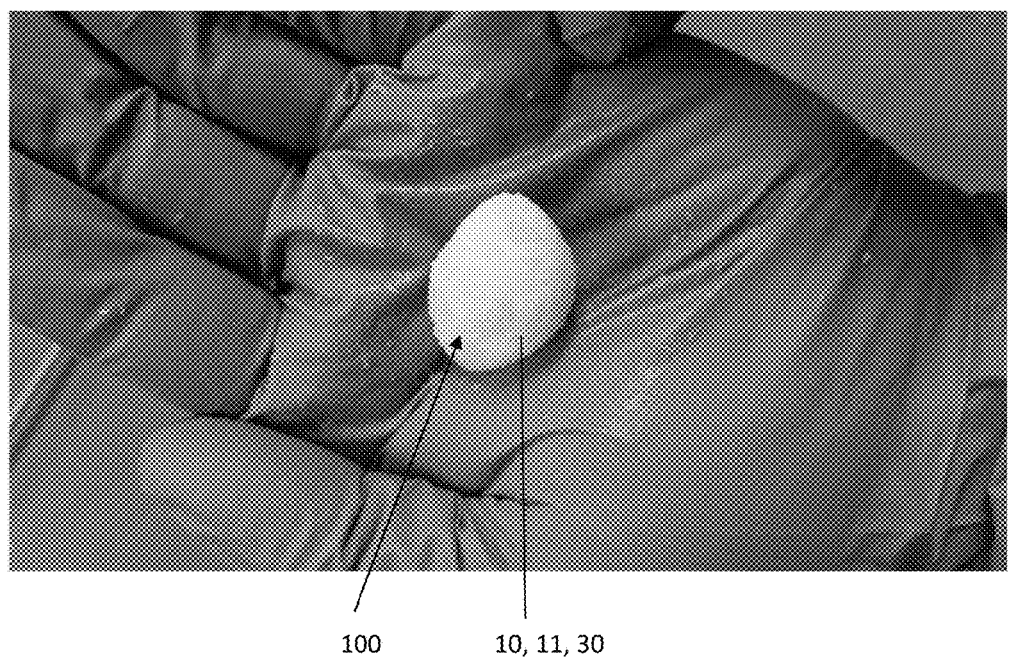
FIG. 6B is a photograph of the cohesive bone composition molded into a ball or sphere.

With reference to FIGS. 1-6A, 6B, photographs of the cohesive bone composition are illustrated. With reference to FIG. 1, a finished moldable bone composition 10 is shown in a container 20 sealed in a plastic bag 50. The moldable bone composition 10 has four primary freeze-dried elements as illustrated, a demineralized cortical bone shaving portion 12, a mineralized cortical bone shaving portion 14, a powdered cortical bone portion 16 and crushed cancellous portion 18. These are divided in a particular ratio or proportion such that the moldable bone composition 10, when wetted, can have the osteogenic effect needed for bone repair when applied to a bone defect or bone void. With reference to FIG. 2, the freeze-dried moldable bone composition 10 is shown as well as the bone gel 11 in sealed jars, also a vial of cells 30 including stem cells is shown. The cells 30 are suspended in a fluid in the vial 33. The components have a package insert 40 and are all sealed in packaging 50 as shown in FIG. 1. With reference to FIG. 2, when the moldable composition 10 is taken from the package 50 and laid on a drape as illustrated, the container 20 has the freeze-dried elements in proper proportion as previously discussed. The vial 33 filled with a liquid laden with cells 30 is shown lying adjacent to the container 20 holding the composition 10. The bone gel composition 11 in its container is next to container 20. The physician can then take the vial 33, remove the cap from the vial body 33 and pour the contents directly onto the freeze-dried moldable composition 10 wetting the composition, as shown in FIG. 3 and the bone gel has been placed on the palm of a sterile gloved hand. In FIG. 4, the wetted moldable bone composition 10 is mixed with the bone gel 11. With reference to FIG. 5, once the bone composition 10 has been wetted and mixed with the bone gel composition 11, the physician can mold the cohesive bone composition 100 into any desired shape he needs, as shown in FIGS. 6A and 6B. This is particularly useful when packing a spinal fusion implant or a bone defect or any other component where an osteogenic beneficial enhancement of bone growth is to be encouraged. While in the illustrated embodiment, a vial 33 with fluid laden with cells 30 is shown as the fluid in which the composition 20 is wetted, it is understood that any number of appropriate fluids could be used when wetting the material such as sterile water, lactated Ringer's solution, normal saline, plasma, blood or any other commonly used material such that the freeze-dried composition becomes wetted and is able to be molded into the desired shape.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of manufacturing a cohesive bone composition of a mixture of a moldable bone composition and a bone gel composition comprises the steps of:
    wherein the method of manufacturing a moldable bone composition comprises the steps of:
    cutting cortical bone plates into long pieces;
    shaving the cortical bone plates to form cortical strands or shavings 3 mm or greater in length;
    demineralizing a first portion of the cortical shavings;
    grinding another portion of the cortical shavings; resulting in cortical bone having three portions, a demineralized cortical shavings portion, a mineralized cortical shavings portion and a powered cortical portion;
    cutting and grinding cancellous bone to form a portion of mineralized crushed cancellous bone from a size of 1000 to 1700 microns;
    freeze-drying each portion;
    mixing together all of the portions in a predetermined ratio to form a freeze-dried composition; and
    wherein the method of making a bone gel composition consisting of cortical bone comprises the steps of:
    preparing cortical bone by cutting the cortical bone into pieces, freeze-drying the pieces and then grinding into particles and demineralizing the ground particles and the freeze-drying the demineralized ground particles to form DBM particles;
    autoclaving a volume of the DBM particles mixed with sterile water in a 2:1 ratio by volume for a predetermined time at a pre-set temperature and pressure to form a gelatin;
    cooling the gelatin to form a bone gel composition;
    packaging the resulting bone gel composition; and
    wherein a volume of moldable bone composition is mixed with a volume of the bone gel composition and wetted with a fluid to form the cohesive bone composition.

2. The method of manufacturing a cohesive bone composition of claim 1 further comprises the step of adding a vial of fluid to the packages.

3. The method of manufacturing a cohesive bone composition of claim 2 wherein the vial of fluid can be sterile water, lactated Ringer's solution, normal saline, plasma, blood or any other commonly used material with or without cells added.

* * * * *